(12) United States Patent
Ramadan

(10) Patent No.: US 10,322,023 B1
(45) Date of Patent: Jun. 18, 2019

(54) CERVICAL COLLAR DEVICE FOR APPLYING A CONSTANT UPWARD PUSH FORCE

(71) Applicant: Hossein Ramadan, Marrietta, GA (US)

(72) Inventor: Hossein Ramadan, Marrietta, GA (US)

(*) Notice: Subject to any disclaimer, the term of this patent is extended or adjusted under 35 U.S.C. 154(b) by 0 days.

(21) Appl. No.: 15/927,469

(22) Filed: Mar. 21, 2018

(51) Int. Cl.
*A61F 5/042* (2006.01)
*A61F 5/055* (2006.01)
*A61F 5/01* (2006.01)

(52) U.S. Cl.
CPC .............. *A61F 5/042* (2013.01); *A61F 5/055* (2013.01); *A61F 2005/0197* (2013.01)

(58) Field of Classification Search
CPC .. A61F 5/055; A61F 5/042; A61F 2005/0197; A61H 1/0296; A63B 21/4003; A63B 21/4039; A63B 23/025; A63B 71/1291
See application file for complete search history.

(56) References Cited

U.S. PATENT DOCUMENTS

| | | | |
|---|---|---|---|
| 2,818,063 A | 12/1957 | Smith et al. | |
| 3,220,406 A | 11/1965 | Connelly | |
| 3,285,243 A | 11/1966 | Yellin | |
| 3,285,244 A | 11/1966 | Cottrell | |
| 3,306,284 A | 2/1967 | McKinley | |
| 3,374,785 A | 3/1968 | Gaylord, Jr. | |
| 3,530,853 A | 9/1970 | Bond | |
| 3,696,810 A | 10/1972 | Gaylord, Jr. | |
| 3,915,161 A * | 10/1975 | Shields | A61F 5/055 602/17 |
| 4,401,111 A | 8/1983 | Blackstone | |
| 6,201,425 B1 | 3/2001 | Kartschoke et al. | |
| 7,981,068 B2 | 7/2011 | Thorgilsdottir et al. | |
| 2010/0036301 A1* | 2/2010 | Baldauf | A61G 7/072 602/14 |
| 2010/0307512 A1* | 12/2010 | Krook | A61F 5/56 128/848 |

* cited by examiner

*Primary Examiner* — Kari K Rodriquez
(74) *Attorney, Agent, or Firm* — Mathew L. Grell; Jeffrey C. Watson; Grell & Watson Patent Attorneys LLC

(57) ABSTRACT

A cervical collar device for applying a constant upward push force includes a flexible neck brace and a constant upward push force device. The flexible neck brace includes a top and a bottom with a height therebetween, and a first side and a second side with a length therebetween. The height and the length of the flexible neck brace is configured for placement around a neck of a user. The constant upward push force device is positioned inside said flexible neck brace. The constant upward push force is configured to provide a constant upward push force between said top and said bottom of said flexible neck brace.

16 Claims, 12 Drawing Sheets

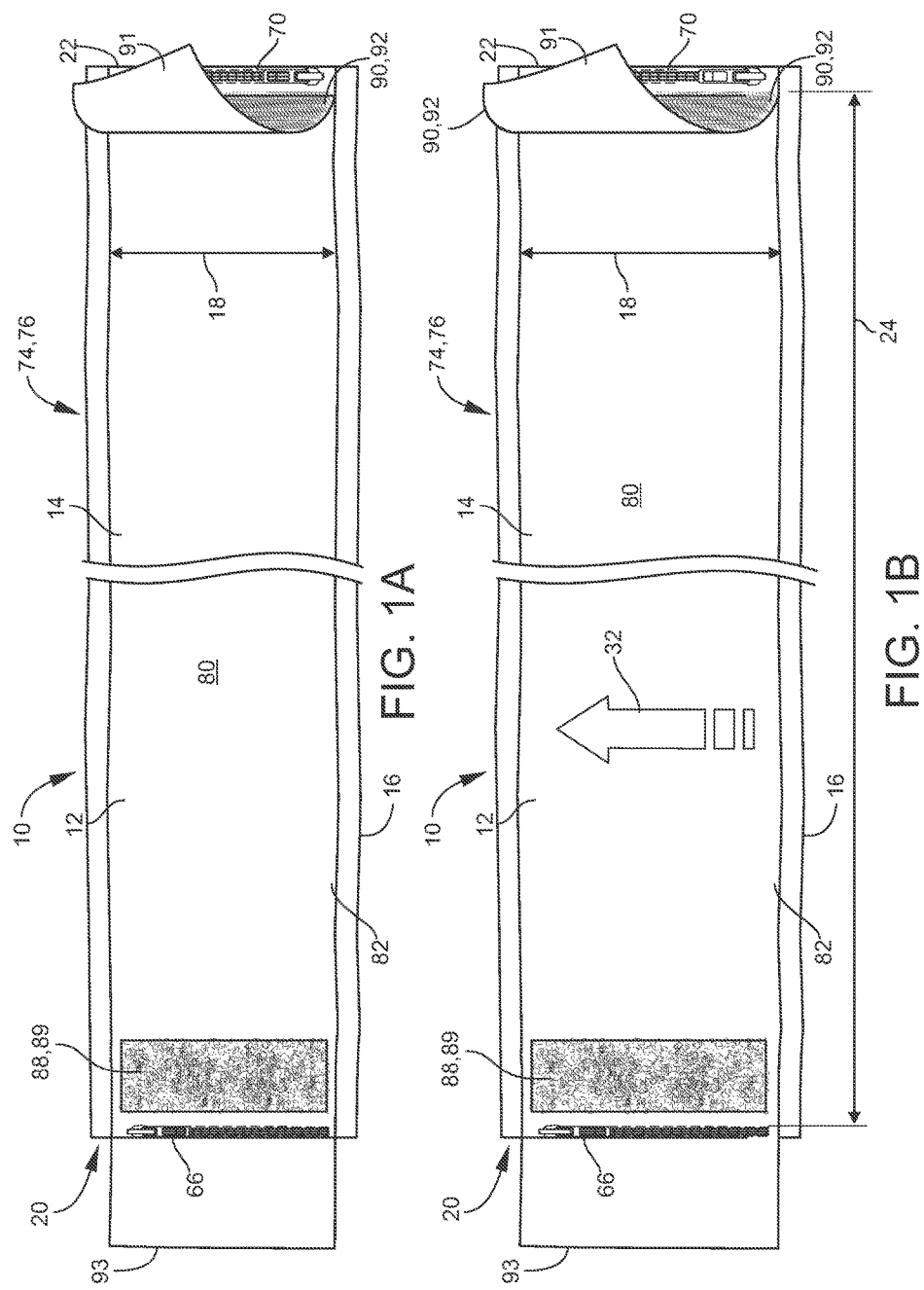

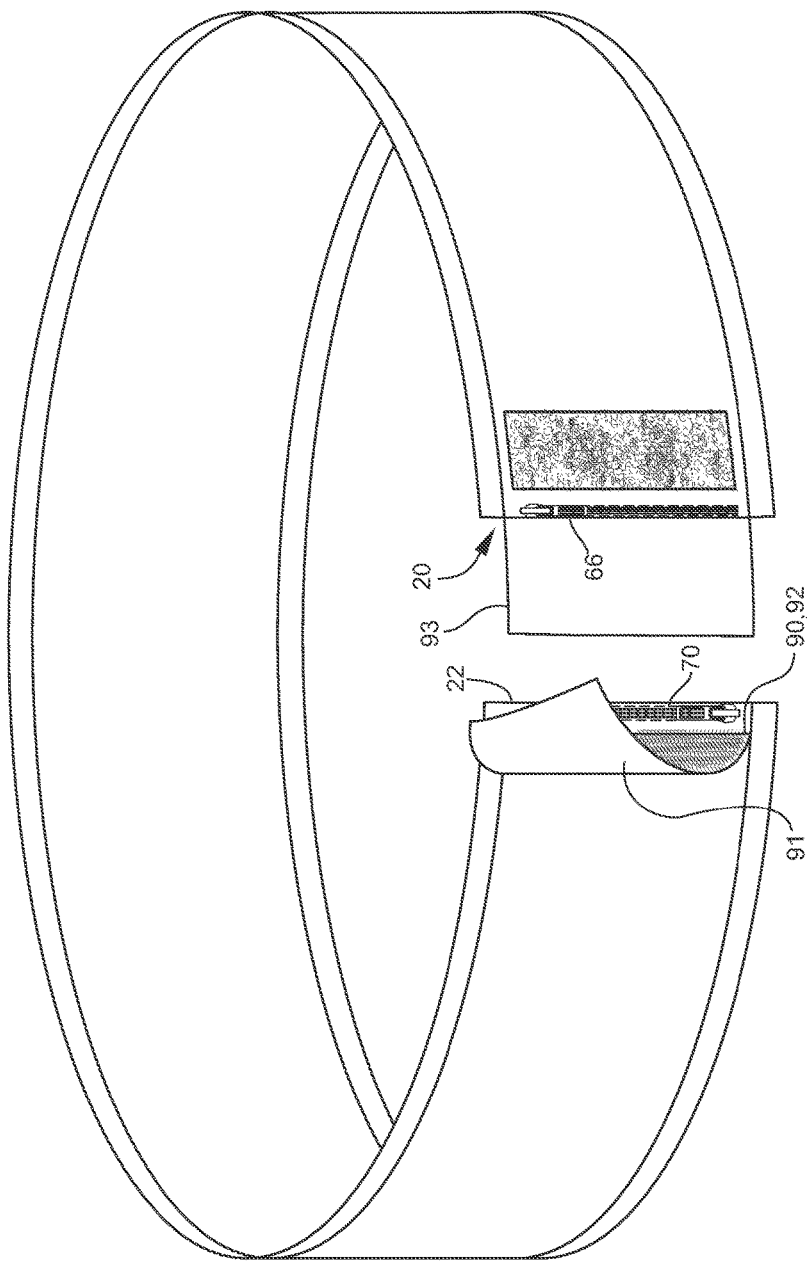

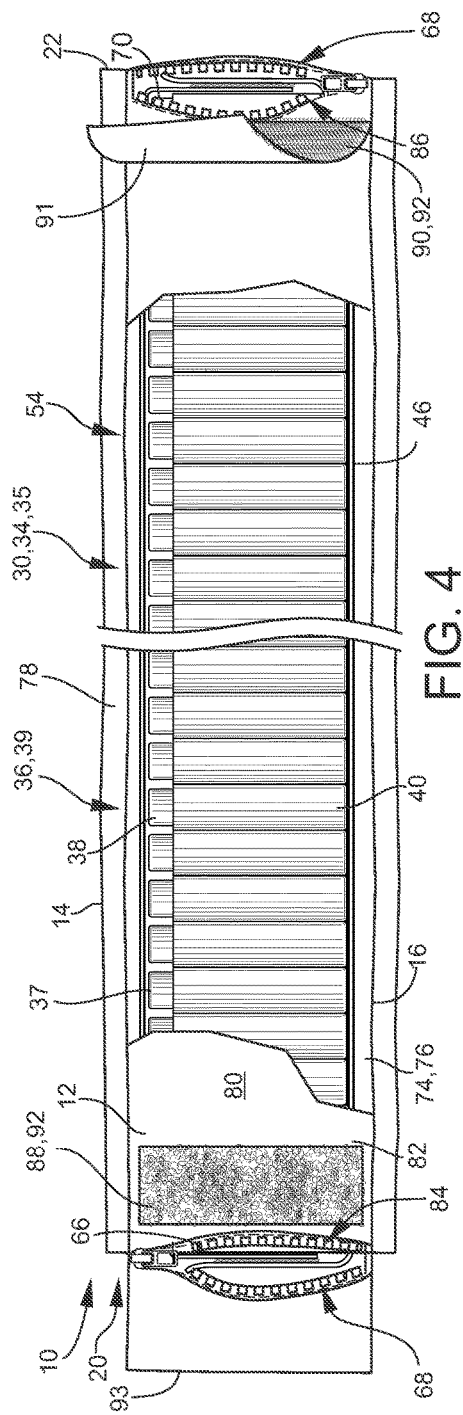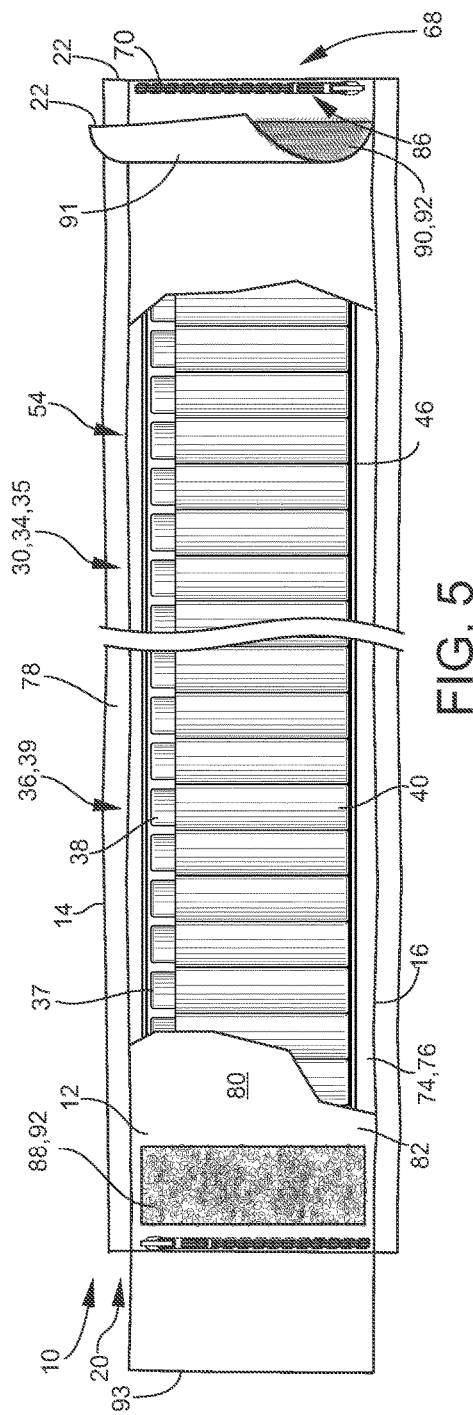

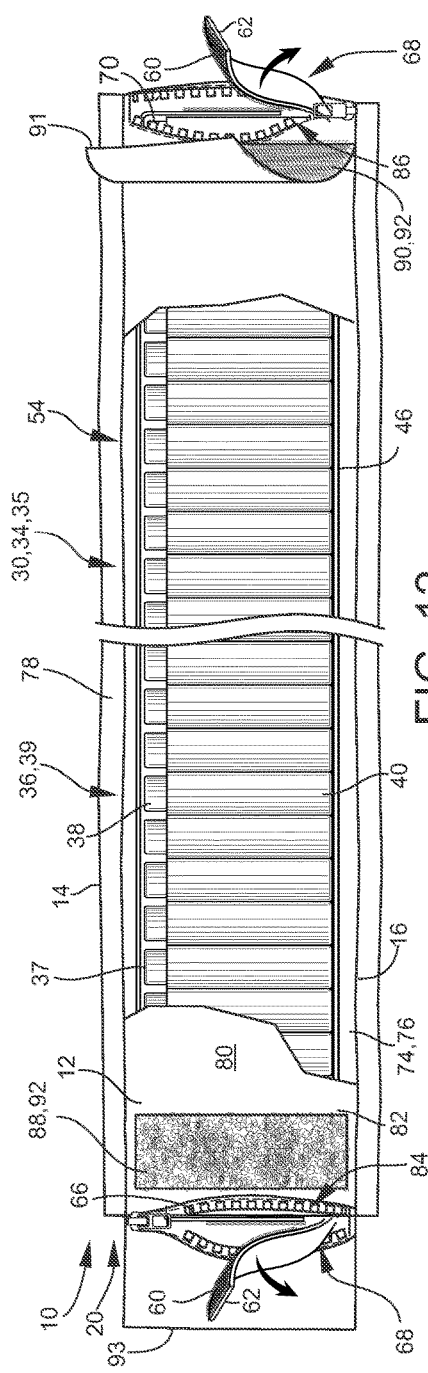
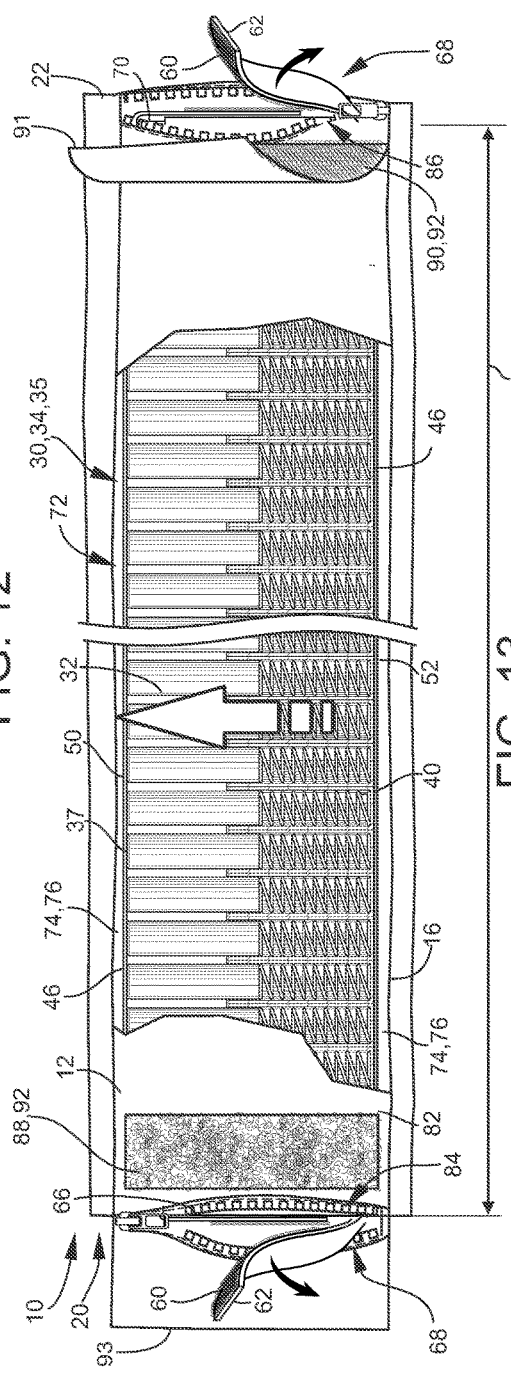

CERVICAL COLLAR DEVICE FOR APPLYING A CONSTANT UPWARD PUSH FORCE

FIELD OF THE DISCLOSURE

The present disclosure relates to a cervical collar device. More specifically, the present disclosure relates to a cervical collar device for providing a constant upward push force for elongation of the neck.

BACKGROUND

A cervical collar, also known as a neck brace, is a medical device commonly used to support a person's neck. It is also used by emergency personnel for those who have had traumatic head or neck injuries. For example, whenever people have a traumatic head or neck injury, they may have a cervical fracture. This makes them at high risk for spinal cord injury, which could be exacerbated by movement of the person and could lead to paralysis or death. A common scenario for this injury would be a person suspected of having whiplash because of a car accident. In order to prevent further injury, such people may have a collar placed by medical professionals until X-rays can be taken to determine if a cervical spine fracture exists. The cervical collar may only stabilize the top seven vertebrae, C1 through C7.

Cervical collars are also commonly used to treat chronic medical conditions. For example, cervical collars may be used therapeutically to help realign the spinal cord and relieve pain, although they are usually not worn for long periods of time. Another use of the cervical collar is for strains, sprains or whiplash. If pain is persistent, the collar might be required to remain attached to help in the healing process. A person may also need a cervical collar or may require a halo fixation device to support the neck during recovery after surgery such as cervical spinal fusion.

Cervical collars typically come in two known forms, a soft collar and a rigid collar. A soft collar is flexible and is the least limiting, but can carry a high risk of further breakage, especially in people with osteoporosis. It can be used for minor injuries or after healing has allowed the neck to become more stable. A range of manufactured rigid collars are also used, usually comprising a firm plastic bi-valved shell secured with Velcro straps and removable padded liners. All of these cervical collars can be used with additional chest and head extension pieces to increase stability.

All the uses of these known cervical collars, whether soft or hard, are almost always limited to just stabilizing the neck and restricting certain movements. However, it may be desirable to utilize the cervical collar for other purposes. The instant disclosure recognizes that one of these purposes may be making the neck taller by applying a constant upward push force at the lower jaw and base of skull via a collar positioned around the neck to cause a stretch and elongation of the neck structures, and may provide benefits, such as elongation of the neck if it is worn for a long enough total used time. And another purpose that is recognized by the instant disclosure may be to provide relief of a muscle spasm and alleviate the pain of a cervical spine disc or pinched nerve by applying a constant upward push force at the lower jaw and base of skull to cause stretching of neck muscle, thus, increasing the spaces between cervical vertebrae and relieving the pressure on the pinched nerve to alleviate the pain. In theory, you can potentially elongate any live organ such as tendons, ligaments, muscles, nerves and vessels by applying a constant pull, or stretch, which will enhance tissue growth, therefore, causing the live tissue to accommodate with the direction of the force (vector) and to grow in the direction of the applied force. This theory has been harnessed successfully in lower extremities by orthopedic surgeons to lengthen the legs. The same principles may apply in different methods, like for the correction of teeth alignments, as in orthodontic dentistry.

Accordingly, the instant disclosure may recognize the discovery that applying a constant upward push force or forces to the lower jaw and base of skull via a collar positioned around the neck to cause a stretch and elongation of the neck structures, and may provide benefits, such as the relief of muscle spasm of the neck, and alleviating the pain caused by a cervical spine disc or a pinched nerve. As another example, the instant disclosure may recognize that applying a constant upward push force or forces to the lower jaw and base of skull via a collar positioned around the neck may also prevent shortening of the neck in older adults with osteoporosis which causes decrease in the height and thickness of the cervical vertebrae. As yet another example, the instant disclosure may recognize that applying a constant upward push force or forces to the lower jaw and base of skull via a collar positioned around the neck to cause a stretch of the neck muscle may relieve muscle spasm of the neck. Therefore the instant disclosure may recognize the clear need for a new improved cervical collar device that may provide two immediate benefits such as a relief of muscle spasm of the neck and alleviation of pain caused by cervical disc or pinched nerve in the neck. In addition, it may provide a long term benefit by promoting elongation and lengthening of the neck if used for long enough total used time.

The instant disclosure of a cervical collar device for providing a constant upward push force to the lower jaw and base of skull via a collar positioned around the neck may be designed to address at least certain aspects of the problems and/or discoveries discussed above.

SUMMARY

Accordingly, in one aspect, the present invention embraces a cervical collar device for applying a constant upward push force to the lower jaw and base of skull via the collar positioned around the neck. The cervical collar device of the instant disclosure may include a flexible neck brace and a constant upward push force device. The flexible neck brace may include a top and a bottom with a height therebetween, and a first side and a second side with a length therebetween. The height and the length of the flexible neck brace may be configured for placement around a user's neck. The constant upward push device may be positioned inside said flexible neck brace. In select embodiments, the constant upward push force device may be inserted into a hollow compartment, which occupies the entire cervical collar, and it is positioned between its front and back sides. The constant upward push force device may be configured to provide a constant upward push force between the top and the bottom of the flexible neck brace.

One feature of the instant cervical collar device may be that the constant upward push force provided by the cervical collar device may promote and enhance growth and elongation of the neck by applying the constant upward push force for stretching of the user's neck.

In select embodiments of the cervical collar device, the constant upward push force device may be accomplished utilizing any forms or shapes of spring or springs mechanism. The constant upward push force device may be, but is clearly not limited thereto, either of two coil springs assemblies, described in detail hereafter: first is a coil springs pistons assembly; and second is a coil springs without pistons assembly. Both coil springs assemblies have the same function and are similar in size and may be used as an alternative to each other or in various combinations. The coil springs piston assembly may be configured to promote and enhance growth and elongation of the neck by applying the constant upward push force for stretching of the user's neck. The coil springs piston assembly may include a plurality of coil spring piston units configured to provide the constant upward push force at a plurality of force locations. In select embodiments, each of the plurality of coil spring piston units may include an upper cylinder piston, a hollow lower cylinder, and a coil spring. Wherein, the upper cylinder piston may slide within the hollow lower cylinder, where the upper cylinder piston and the hollow lower cylinder may contain the coil spring. The coil spring may be configured to bias the upper cylinder piston from the hollow lower cylinder. Whereby, the upper cylinder piston may be configured to slide into the hollow lower cylinder under pressure and compress the coil spring, and the upper cylinder piston may be configured to slide out of the hollow lower cylinder when the pressure is released by the bias provided by the coil spring. In select embodiments, the coil springs piston assembly may comprise 20 to 40 coil spring piston units configured to provide the constant upward push force at a corresponding 20 to 40 force locations. In select embodiments, the constant upward push force provided by the coil springs piston assembly may be from 5-15 lb PSI, or more, or as much push force as required to fulfill its desired function.

In other select embodiments of the cervical collar device, the constant upward push force device may be a coil springs without pistons assembly. The coil springs without piston assembly may be configured to promote and enhance growth and elongation of the neck by applying the constant upward push force for stretching of the user's neck. The coil springs without pistons assembly may include a plurality of coil spring without piston units configured to provide the constant upward push force at a plurality of force locations. In select embodiments, each of the plurality of coil spring without piston units may include a hollow lower cylinder, and an extended coil spring. Unlike the coil springs piston unit, no upper cylinder piston is included and the extended coil spring may have double the length of the coil spring in the coil spring piston unit in order to compensate for the length of the absent upper cylinder piston. Wherein, the extended coil spring may be positioned within the hollow lower cylinder, where the extended coil spring is configured to bias out of the hollow lower cylinder, whereby the extended coil spring is configured to compress into the hollow lower cylinder under pressure, and the extended coil spring is configured to extend out of the hollow lower cylinder when the pressure is released. In select embodiments, the coil springs without piston assembly may comprise 20 to 40 coil spring without piston units configured to provide the constant upward push force at a corresponding 20 to 40 force locations. In select embodiments, the constant upward push force provided by the coil springs without piston assembly may be from 5-15 lb PSI, or more, or as much push force as required to fulfill its desired function.

In other select embodiments of the instant cervical collar device, the coil springs piston assembly or coil spring without pistons assembly may include a flexible housing. The flexible housing may be configured to hold each of the coil spring piston units or coil springs without piston units. In select embodiments, the flexible housing of the constant upward push force device may include a plurality of partitions configured for confining each of the coil spring piston units or coil spring without piston units between each partition. In other select embodiments, the flexible housing may include a top strip belt and a bottom strip belt. The top strip belt and the bottom strip belt may be configured to connect together around the flexible housing. Where, in combination, the top strip belt and the bottom strip belt may be configured to hold the plurality of coil spring piston units or coil spring without piston units in a compressed position before insertion into the flexible neck brace. In select embodiments, the top strip belt may include a top fastener at or along portions of both ends and the bottom strip belt may include a bottom fastener at or along portions near both ends. In combination, the top fasteners may be configured to attach to the bottom fasteners at their respective ends for holding the plurality of coil spring piston units or coil spring without piston units in the compressed position before insertion into the flexible neck brace. In select embodiments, the top fastener and the bottom fastener may be hook and loop type fasteners.

Another feature of the instant cervical collar device may be the inclusion of a first opening and/or a second opening. The first opening may be located on or approximate the first side of the flexible neck brace. The first opening may be configured for accessing a compartment inside of the flexible neck brace. The second opening may be located on or approximate the second side of the flexible neck brace. The second opening may be configured for accessing the compartment inside of the flexible neck brace. This compartment that is accessible via the first and/or second openings may be sized to receive the constant upward push force device, including the coil spring piston assembly or coil spring without piston assembly. Wherein, the constant upward push force device can be inserted into and out of the compartment inside the flexible neck brace via the first opening or the second opening. In select embodiments, the first opening may be a first zipper and/or the second opening may be a second zipper.

Another feature of the instant cervical collar device may be that when the constant upward push force device is inserted inside the compartment of the flexible neck brace, the flexible neck brace may be configured for placement around a user's neck, where each of the top fasteners are configured to be released from each of the bottom fasteners via the first opening with the first zipper and the second opening with the second zipper, thereby releasing the top strip belt from the bottom strip belt and releasing the plurality of coil spring piston units or coil spring without piston units from the compressed position to an expanded position for providing the constant upward push force.

In select embodiments, the flexible neck brace may include a stretchable fabric with a foam lining. This stretchable fabric with the foam lining may be positioned on an inner side, the top, and the bottom of the soft collar.

In select embodiments, the flexible neck brace may include a hard, porous and flexible plate on an outer side and ends. This plate may include the first opening with the first zipper on the first side configured for accessing the compartment inside the flexible neck brace. This plate may also include the second opening with the second zipper on the second side configured for accessing the compartment inside the flexible neck brace.

Another feature of the instant cervical collar device may be the inclusion of a first fastener and a second fastener. The first fastener may be approximate the first side. In select embodiments, the first fastener may be located on the flexible plate approximate the first side at the medial (inner) aspect of the first zipper. The second fastener may be located on a flap approximate the second side. In select embodiments, the second fastener may be adhered to the back of the flap located approximate the second side at the medial (inner) aspect of the second zipper. Whereby, when the user wraps the flexible neck brace around the neck of the user, the flap with the second fastener may be configured to extend over the second zipper, the second side, and the first side with the first zipper, where it may be attached to the first fastener for securing the flexible neck brace around the neck of the user. In select embodiments, the first fastener and the second fastener may be hook and loop type fasteners configured to secure to one another.

Another feature of the instant cervical collar device may be the inclusion of a protective tab. The protective tab may be positioned on the first side. The protective tab may be configured for protecting the neck of the user from the first end with the first zipper and/or the second side with the second zipper. Whereby, when the user wraps the flexible neck brace around the neck of the user, the protective tab may be configured to extend behind the first side with the first zipper and the second side with the second zipper for protecting the neck of the user Another feature of the instant cervical collar device may be that the flexible neck brace may be configured to be worn around the user's neck by slightly compressing it with the user's hands and placing it around the neck.

Another feature of the instant cervical collar device may be that the flexible neck brace may be configured to be placed around the neck on top of clavicle bones and shoulders of the user, which are non-movable, whereby the flexible neck brace may provide the constant upward push force on a lower jaw, a mastoid bone and a base of skull at the various force locations, thereby causing the cervical spine structures, including the vertebrae, all neck muscles, nerves and vessels to be under a constant stretch which may with time promote and enhance a potential growth and lengthening of the cervical structure, especially in children and young adults, and also may prevent the shortening of the neck caused by osteoporosis of cervical vertebrae in older adults.

Another feature of the instant cervical collar device may be that it can provide relief of muscle spasm of the neck.

Another feature of the instant cervical collar device may be that it can alleviate pain caused by a cervical spine disc or a pinched nerve.

Another feature of the instant cervical collar device may be that it can promote lengthening of the neck in children and young adults.

Another feature of the instant cervical collar device may be that it can prevents shortening of the neck.

Another feature of the instant cervical collar device may be that it can prevent shortening of the neck caused by osteoporosis in older adults.

Another feature of the instant cervical collar device may be that it can relieve muscle spasm of the neck by stretching the muscles.

Another feature of the instant cervical collar device may be that it can alleviate the pain caused by cervical disc or pinched nerve by stretching the cervical spine and increasing the spaces between the vertebrae, thus, relieving the pressure on the nerve.

Another feature of the instant cervical collar device may be that the cervical collar device does not require any power source to function.

Another feature of the instant cervical collar device may be that the cervical collar device has no need for maintenance.

Another feature of the instant cervical collar device may be that the cervical collar device may be washable and dryable.

Another feature of the instant cervical collar device may be that the constant upward push force device may be replaceable.

In another aspect, the instant disclosure may provide a method of promoting and enhancing growth and elongation of the neck by applying a constant upward push force for stretching of the user's neck. This method of promoting and enhancing growth and elongation of the neck by applying a constant upward push force for stretching of the user's neck may generally include the step of providing the instant cervical collar device in any of the various embodiments shown and/or described herein, including at least the flexible neck brace with the constant upward push force device. As such, the instant method of promoting and enhancing growth and elongation of the neck by applying a constant upward push force for stretching of the user's neck may also include the step of positioning the cervical collar device around a user's neck for providing the constant upward push force.

In select embodiments of the instant method of promoting and enhancing growth and elongation of the neck by applying a constant upward push force for stretching of the user's neck, the step of positioning the cervical collar device around a user's neck for providing the constant upward push force may include the steps of: inserting the constant upward push force device, which may contain the coil springs piston assembly or the coil springs without piston assembly in the compressed position, inside the compartment via the first opening or the second opening in a compressed position; releasing the top strip belt from the bottom strip belt via access through the first opening and second opening thereby releasing the coil springs piston assembly or coil spring without piston assembly from the compressed position to an expanded position; and wrapping the flexible neck brace around the user's neck on top of clavicle bones and shoulders of the user, which are non-movable, whereby the flexible neck brace provides the constant upward push force on the lower jaw, the mastoid bone and the base of skull at the various force locations, thereby causing the cervical spine structures, including the vertebrae, all neck muscles, nerves and vessels to be under a constant stretch which will with time promote and enhance a potential growth and lengthening of the cervical structure in children and young adults, and also prevents the shortening of the neck due to osteoporosis of cervical vertebrae in older adults.

The foregoing illustrative summary, as well as other exemplary objectives and/or advantages of the invention, and the manner in which the same are accomplished, are further explained within the following detailed description and its accompanying drawings.

BRIEF DESCRIPTION OF THE DRAWINGS

The present apparatuses, systems and methods will be better understood by reading the Detailed Description with reference to the accompanying drawings, which are not necessarily drawn to scale, and in which like reference numerals denote similar structure and refer to like elements throughout, and in which:

FIG. 1A is a front view of the cervical collar device according to select embodiments of the instant disclosure;

FIG. 1B is a front view of the cervical collar device of FIG. 1A showing the constant upward push force;

FIG. 1C is a top perspective view of the cervical collar device of FIG. 1A being wrapped around end to end in position for securing the first fastener with the second fastener;

FIG. 4 is a front view of the cervical collar device according to select embodiments of the instant disclosure with the zippers open and the plate partially broken away to show the coil springs piston assembly or the coil spring without piston assembly in a compressed position;

FIG. 5 is a front view of the cervical collar device of FIG. 4 with the zippers closed;

FIG. 12 is a front view of the cervical collar device according to select embodiments of the instant disclosure with the zippers open and the bottom strip belt being disconnected from the top strip belt, and the plate partially broken away to show the coil springs piston assembly or coil spring without piston assembly in a compressed position;

FIG. 13 is a front view of the cervical collar device of FIG. 12 with the zippers open and the bottom strip belt disconnected from the top strip belt, and the plate partially broken away to show the coil springs piston assembly or coil spring without piston assembly in an expanded position.

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

DETAILED DESCRIPTION

Referring now to FIGS. 1-14, in describing the exemplary embodiments of the present disclosure, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples and are merely examples among other possible examples.

Figure 2:
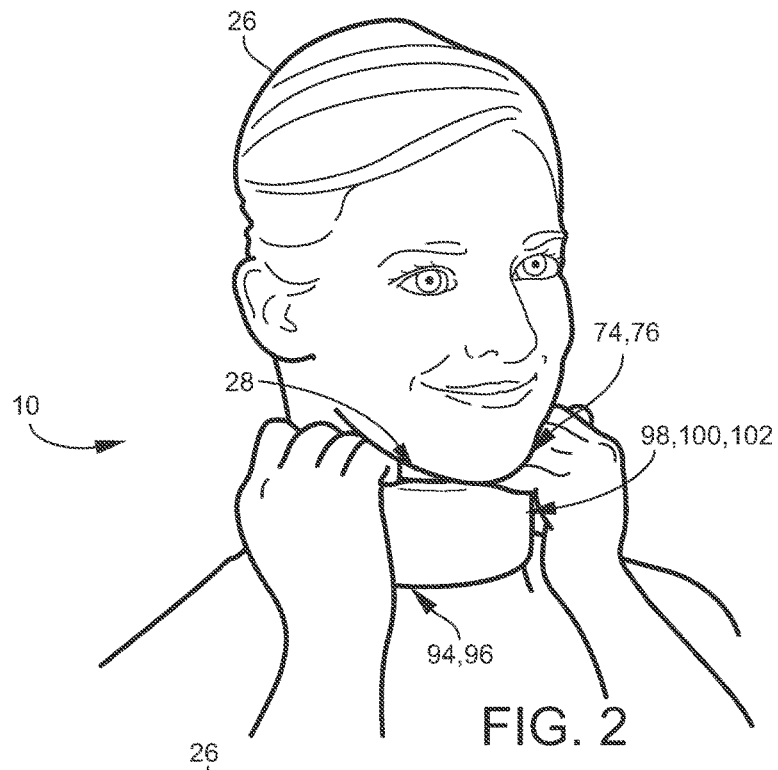
FIG. 2 is an environmental perspective view of the cervical collar device according to select embodiments of the instant disclosure being wrapped around the user's neck and compressed with the user's hands for positioning.
Figure 3:
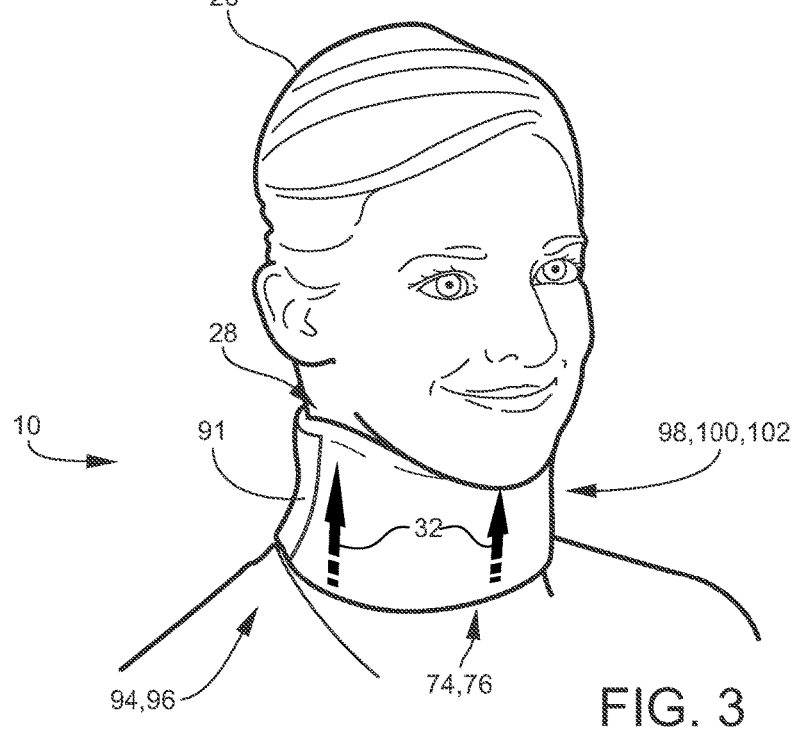
FIG. 3 is an environmental perspective view of the cervical collar device of FIG. 2 being positioned around the user's neck and applying the constant upward push force.

Referring now to FIGS. 1-13, in a possibly preferred embodiment, the present disclosure overcomes the above-mentioned disadvantages and meets the recognized need for such an apparatus or method by providing of cervical collar device 10. Cervical collar device 10 may be for applying constant upward push force 32. Cervical collar device 10 may generally include flexible neck brace 12 and constant upward push force device 30. Flexible neck brace 12 may include top 14 and bottom 16 with height 18 therebetween, and first side 20 and second side 22 with length 24 therebetween. Height 18 and length 24 of flexible neck brace 12 may be configured for placement around neck 28 of user 26, as shown in FIGS. 2-3. The constant upward push force device 30 may be positioned in or on flexible neck brace 12. The constant upward push force device 30 may be configured to provide constant upward push force 32 between top 14 and bottom 16 of flexible neck brace 12.

Constant upward push force 32 provided by cervical collar device 10 may promote and enhance growth and elongation of neck 28 by applying constant upward push force 32 for stretching of the neck 28 of the user 26. Constant upward push force device 30 may be any device, mechanism, machine, the like, etc. configured to provide constant upward push force 32 to cervical collar device 10. In select embodiments, as shown in the Figures, constant upward push force device 30 may include coil springs pistons assembly 34 or coil springs without piston assembly 35. Coil springs piston assembly 34 or coil springs without piston assembly 35 may be configured to promote and enhance growth and elongation of the neck 28 by applying constant upward push force 32 for stretching of the user's neck 28. Coil springs piston assembly 34 or coil springs without piston assembly 35 may include a plurality of coil spring piston units 36 (see FIG. 6A) or coil spring without piston units 39 (see FIG. 6B) configured to provide constant upward push force 32 at plurality of force locations 37.

Figure 6A:
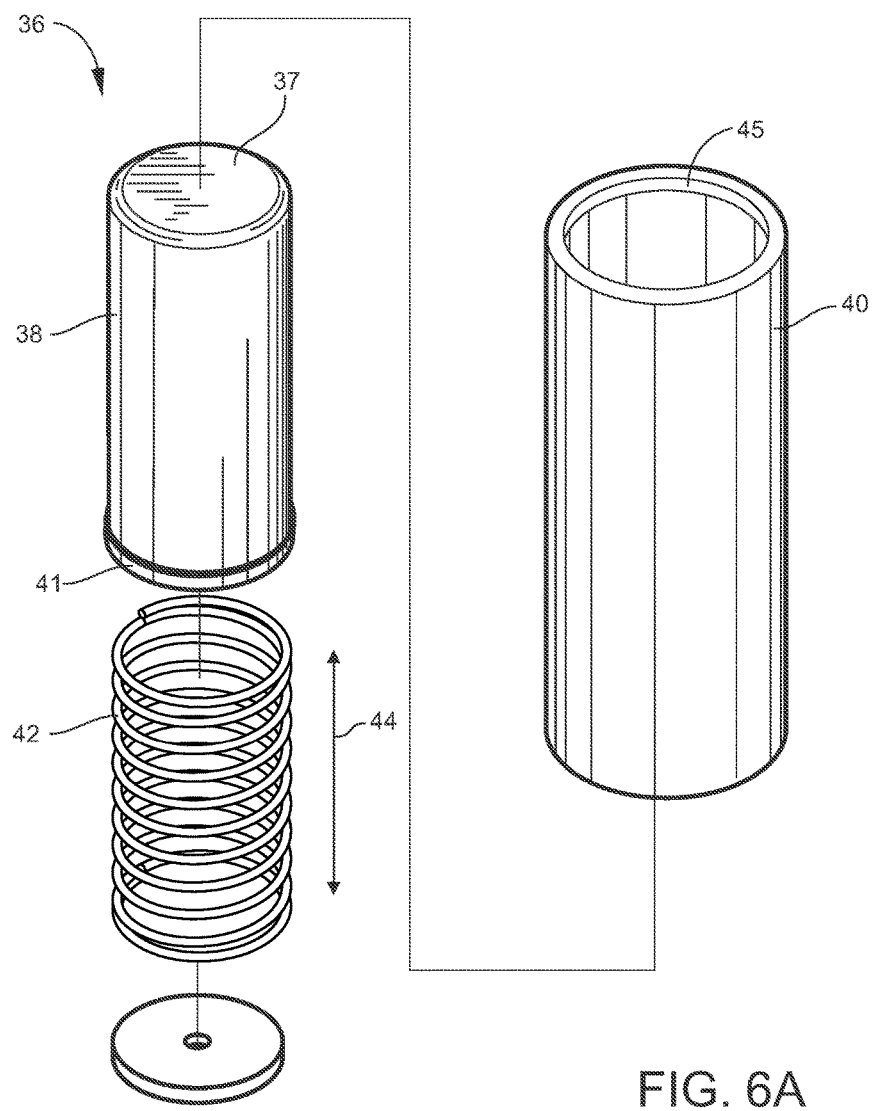
FIG. 6A is a disassembled perspective view of a coil spring piston unit for the coil spring piston assembly according to select embodiments of the instant disclosure.

Referring now specifically to FIG. 6A, in select embodiments, each of the plurality of coil spring piston units 36 for coil spring piston assembly 34 may include upper cylinder piston 38, hollow lower cylinder 40, and coil spring 42.

Upper cylinder piston 38 may slide within hollow lower cylinder 40, where upper cylinder piston 38 and hollow lower cylinder 40 may contain coil spring 42. Hollow lower cylinder 40 may include ridge 45, notch, groove the like etc., configured to hold upper cylinder piston 38 within hollow lower cylinder 40 via a corresponding ridge 41, notch, groove, the like etc. at the end of upper cylinder piston 38. Upper cylinder piston 38 and hollow lower cylinder 40 may be light weight devices made of plastic, metal or the like. Coil spring 42 may be configured to have bias 44 for biasing upper cylinder piston 38 from hollow lower cylinder 40. Coil spring 42 may be any spring or like device configured for biasing upper cylinder piston 38 from hollow lower cylinder 40. Coil spring 42 may be made of a non-rusting metal such as steel or copper. Whereby, upper cylinder piston 38 may be configured to slide into hollow lower cylinder 40 under pressure and compress coil spring 42, and upper cylinder piston 38 may be configured to slide out of hollow lower cylinder 40 when the pressure is released by the bias 44 provided by coil spring 42. In select embodiments, coil springs piston assembly 34 may comprise 20 to 40 coil spring piston units 36 configured to provide constant upward push force 32 at a corresponding 20 to 40 force locations 37. In select embodiments, the constant upward push force 32 provided by the coil springs piston assembly 34 may be from 5-15 lb PSI, or more, or as much force as required to fulfill its desired functions.

Figure 6B:
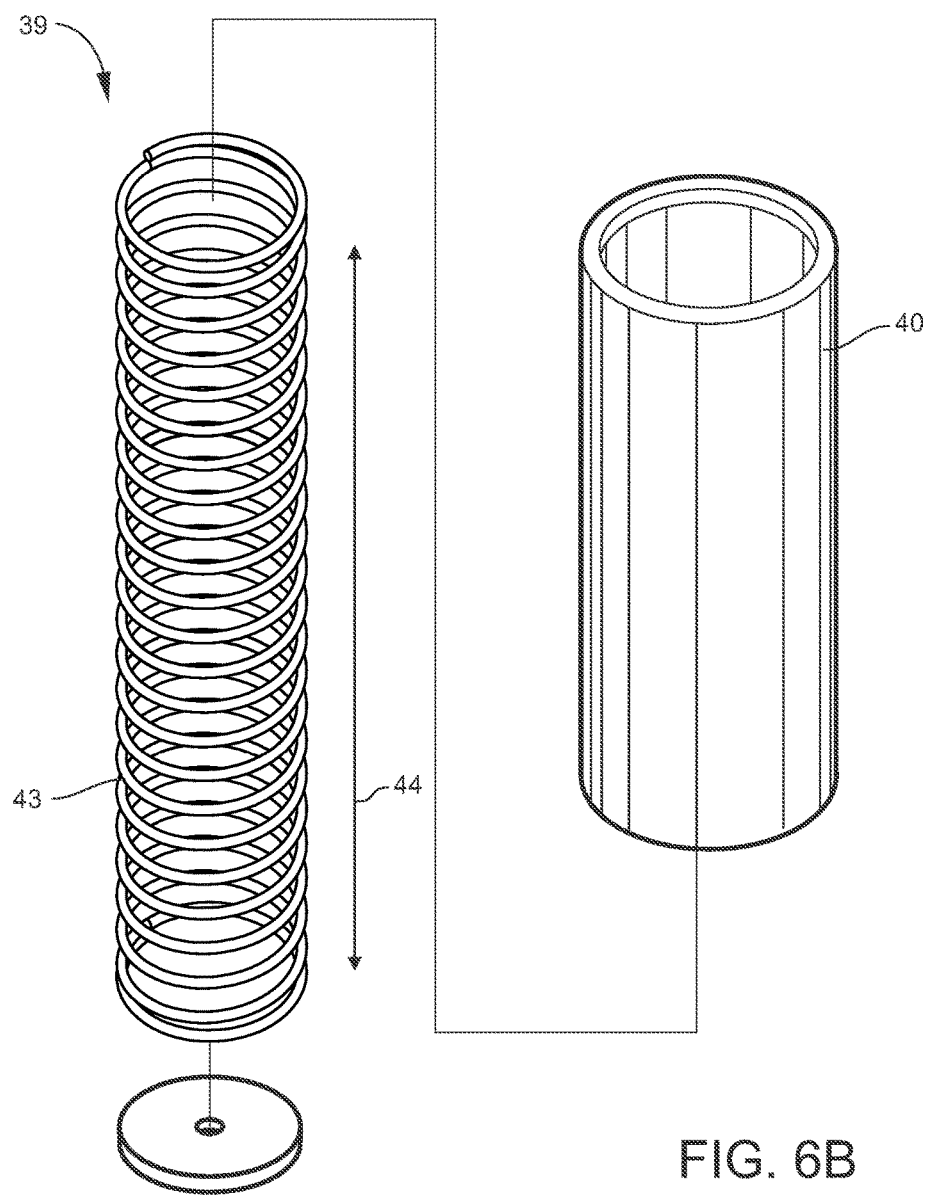
FIG. 6B is a disassembled perspective view of a coil spring without piston unit for the coil spring without piston assembly according to select embodiments of the instant disclosure.

Referring now specifically to FIG. 6B, in select embodiments, each of the plurality of coil spring without piston units 39 for coil spring without piston assembly 35 may include hollow lower cylinder 40, and extended coil spring 43. Extended coil spring 43 may slide within hollow lower cylinder 40. Hollow lower cylinder 40 may be a light weight device made of plastic, metal or the like. Extended coil spring 43 may be configured to have bias 44 for biasing the top of extended coil spring 43 from the bottom of hollow lower cylinder 40. Extended coil spring 43 may be any spring or like device configured for the top of extended coil spring 43 from the bottom of hollow lower cylinder 40. Extended coil spring 43 may be extended from coil spring 42 of coil spring piston unit 36 to make up for the distance of upper cylinder piston 38. Extended coil spring 43 may be made of a non-rusting metal such as steel or copper. Whereby extended coil spring 43 may be configured to compress into hollow lower cylinder 40 under pressure, and extended coil spring 43 may be configured to extend out of hollow lower cylinder 40 when the pressure is released. In select embodiments, coil springs without piston assembly 35 may comprise 20 to 40 coil spring without piston units 39 configured to provide the constant upward push force at a corresponding 20 to 40 force locations. In select embodiments, the constant upward push force provided by the coil springs without piston assembly 35 may be from 5-15 lb psi, or more, or as much force as required to fulfill its desired functions.

Referring now to FIGS. 4-5 and 7-13, flexible housing 46 may optionally be included with coil springs piston assembly 34 or coil spring without pistons assembly 35. Flexible housing 46 may be for containing the plurality of coil spring piston units 36 or coil spring without piston units 39 while allowing each of the coil spring piston units 36 or coil spring without piston units 39 to compress and extend for providing constant upward push force 32. Flexible housing 46 may allow for coil spring piston assembly 34 or coil springs without piston assembly 35 to be taken in and out of flexible neck brace 12, as shown in FIGS. 7-13. Flexible housing 46 may be configured to hold each of the coil spring piston units 36 or coil spring without piston units 39. In select embodiments, as shown in FIGS. 7-11, flexible housing 46 may include a plurality of partitions 48 configured for confining each of the coil spring piston units 36 or coil spring without piston units 39 between each partition 48 within flexible housing 46. Partitions 48 may be any material, fabric, plastic, device, devices, or mechanisms configured to confine each of the coil spring piston units 36 or coil spring without piston units 39 between each partition 48 within flexible housing 46. Referring now to FIGS. 7-13, flexible housing 46 may include top strip belt 50 and bottom strip belt 52. Top strip belt 50 and the bottom strip belt 52 may be configured to connect together around flexible housing 46. In combination, top strip belt 50 and bottom strip belt 52 may be configured to hold the plurality of coil spring piston units 36 or coil spring without piston units 39 in compressed position 54 before insertion into flexible neck brace 12. Top strip belt 50 and bottom strip belt 52 may be made of any desired material configured to connect together around flexible housing 46 and hold the plurality of coil spring piston units 36 or coil spring without piston units 39 in compressed position 54. In select embodiments, top strip belt 50 may include top fastener 56 at or along portions near both ends 58 of top strip belt 50. Likewise, bottom strip belt 52 may include bottom fastener 60 at or along portions near both ends 62 of bottom strip belt 52. In combination, top fasteners 56 may be configured to attach to bottom fasteners 60 at their respective ends 58 and 62 for holding plurality of coil spring piston units 36 or coil spring without piston units 39 in compressed position 54 before insertion into flexible neck brace 12. In select embodiments, as shown in the Figures, top fastener 56 and bottom fastener 60 may be hook and loop type fasteners 64. In these hook and loop type fastener 64 embodiments of top fasteners 56 and bottom fasteners 60, the hoop component of hook and loop type fastener 64 may be positioned on the inside of bottom strip belt 52 near ends 62, and the loop component of hook and loop type fastener 64 may be positioned on the outside of top strip belt 50 near ends 58, or vice versa.

Referring now to FIGS. 1A, 1B, 1C, 4, 5, 7 and 12-13, first opening 84 with first zipper 66 and/or second opening 86 with second zipper 70 may be included with flexible neck brace 12. First opening 84 with first zipper 66 may be located on or approximate first side 20 of flexible neck brace 12, including on the thickness portion of first side 20, as shown in the Figures. First opening 84 with first zipper 66 may be configured for accessing compartment 68 inside of flexible neck brace 12. Second opening 86 with second zipper 70 may be located on or approximate second side 22 of flexible neck brace 12, including on the thickness portion of second side 22. Second opening 86 with second zipper 70 may be configured for accessing compartment 68 inside of flexible neck brace 12. Compartment 68 that is accessible via first and/or second openings 84, 86 may be sized to receive coil springs piston assembly 34 or coil spring without piston assembly 35. Wherein, coil springs piston assembly 34 or coil spring without piston assembly 35 can be inserted into and out of compartment 68 inside flexible neck brace 12 via first zipper 66 and/or second zipper 70. First opening 84 with first zipper 66 and/or second opening 86 with second zipper 70 may be any opening or aperture configured to receive coil springs piston assembly 34 or coil spring without piston assembly 35 into and out of compartment 68 inside flexible neck brace 12, including, but not limited to, zippered openings, hook and loop type fastener openings, snaps, buttons, the like, etc.

Figure 7:
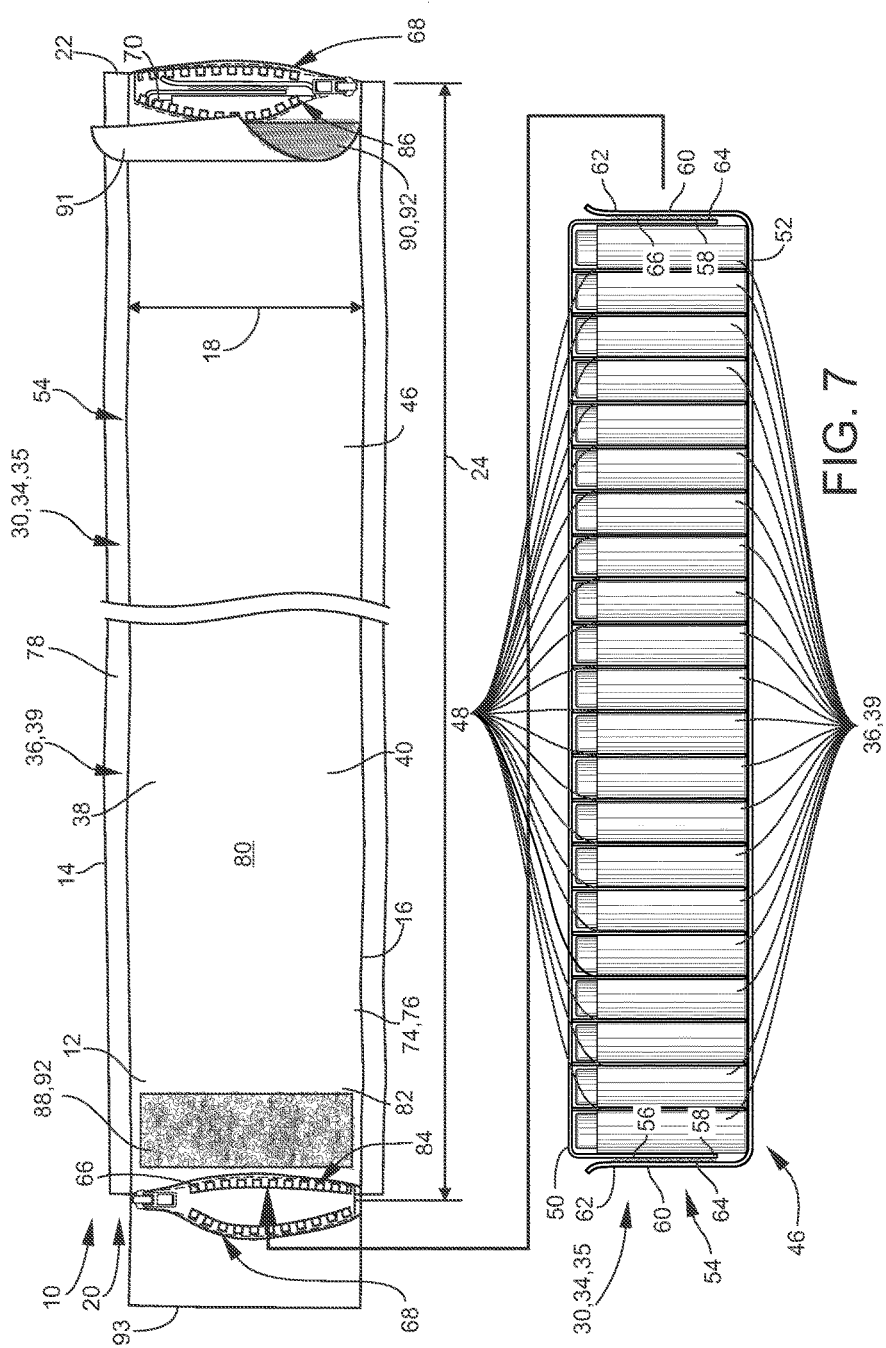
FIG. 7 is a disassembled front view of the cervical collar device according to select embodiments of the instant disclosure with the coil springs piston assembly or the coil spring without piston assembly being removable and insertable into the compartment of the flexible neck brace via the first and/or second zippers.
Figure 8:
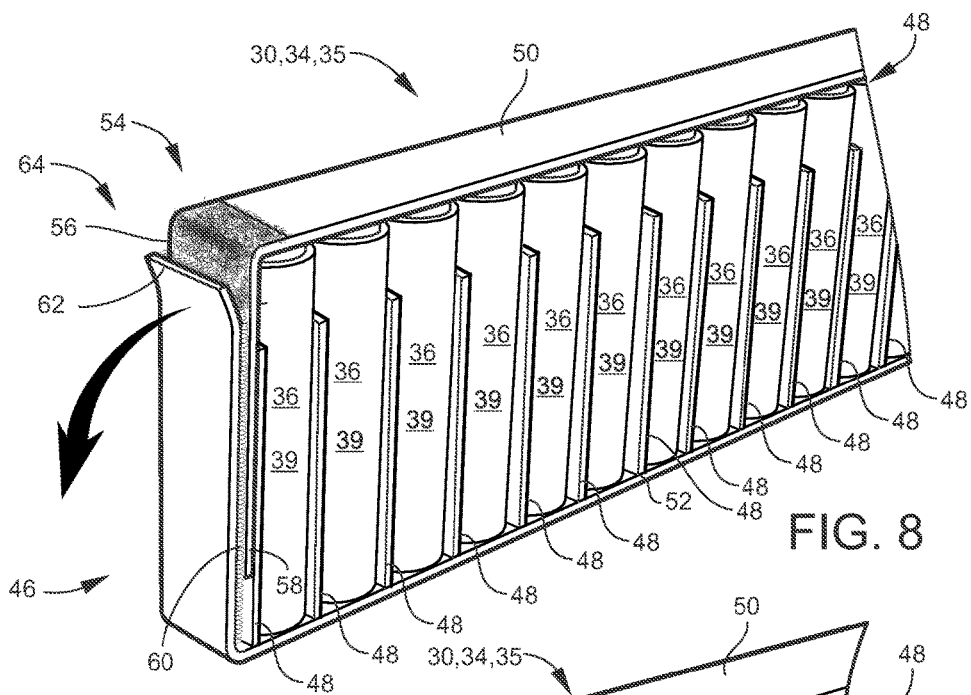
FIG. 8 is a partial perspective view of the coil springs piston assembly or coil spring without piston assembly according to select embodiments of the instant disclosure with the housing holding the coil spring piston units or coil spring without piston units in a compressed position via the top strip belt being fastened to the bottom strip belt.
Figure 9:
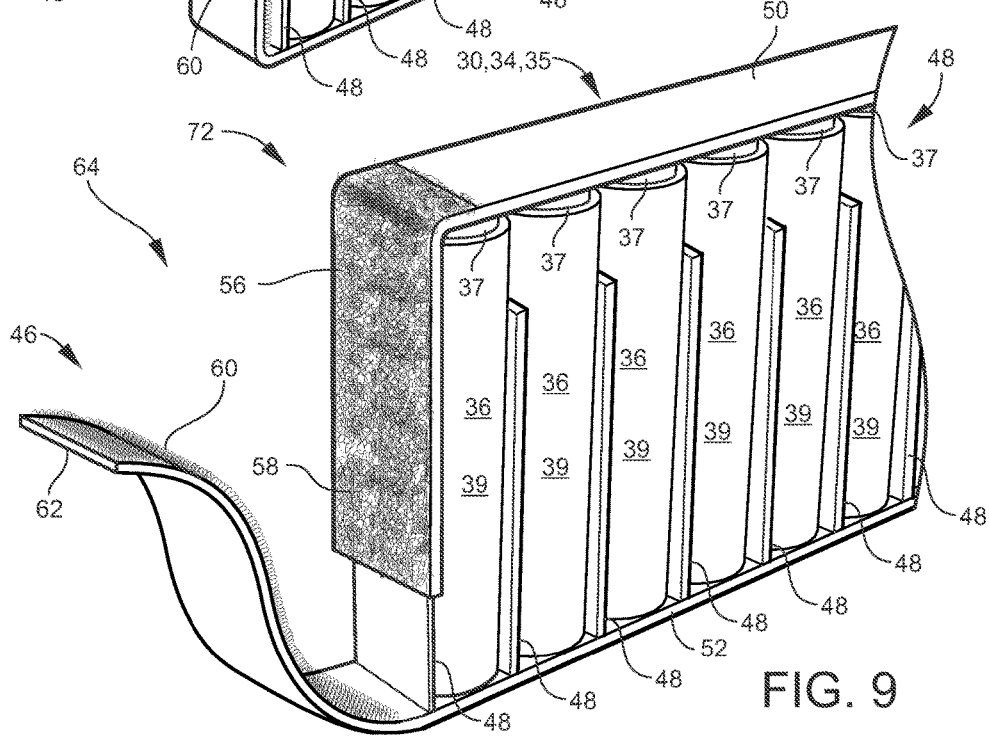
FIG. 9 is a partial perspective view of the coil springs piston assembly or coil spring without piston assembly of FIG. 8 with the bottom strip belt being disconnected from the top strip belt.
Figure 10:
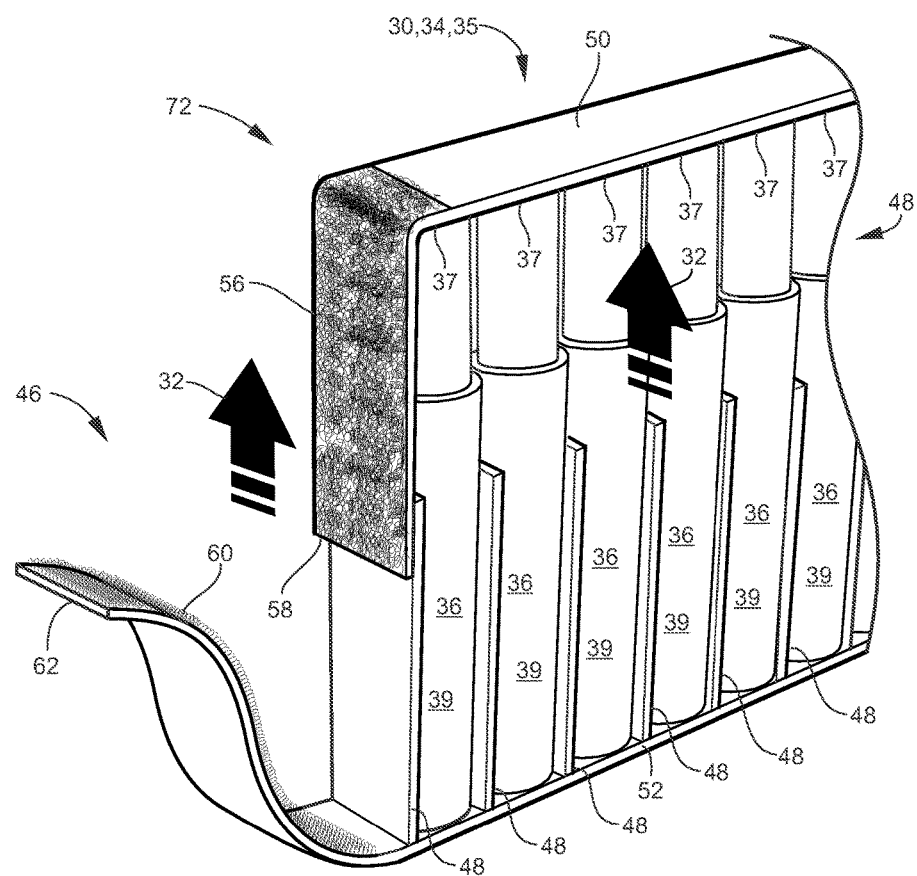
FIG. 10 is a partial perspective view of the coil springs piston assembly or coil spring without piston assembly of FIG. 8 with the bottom strip belt being disconnected from the top strip belt and the coil spring piston units or coil spring without piston units extending to an expanded position.
Figure 11:
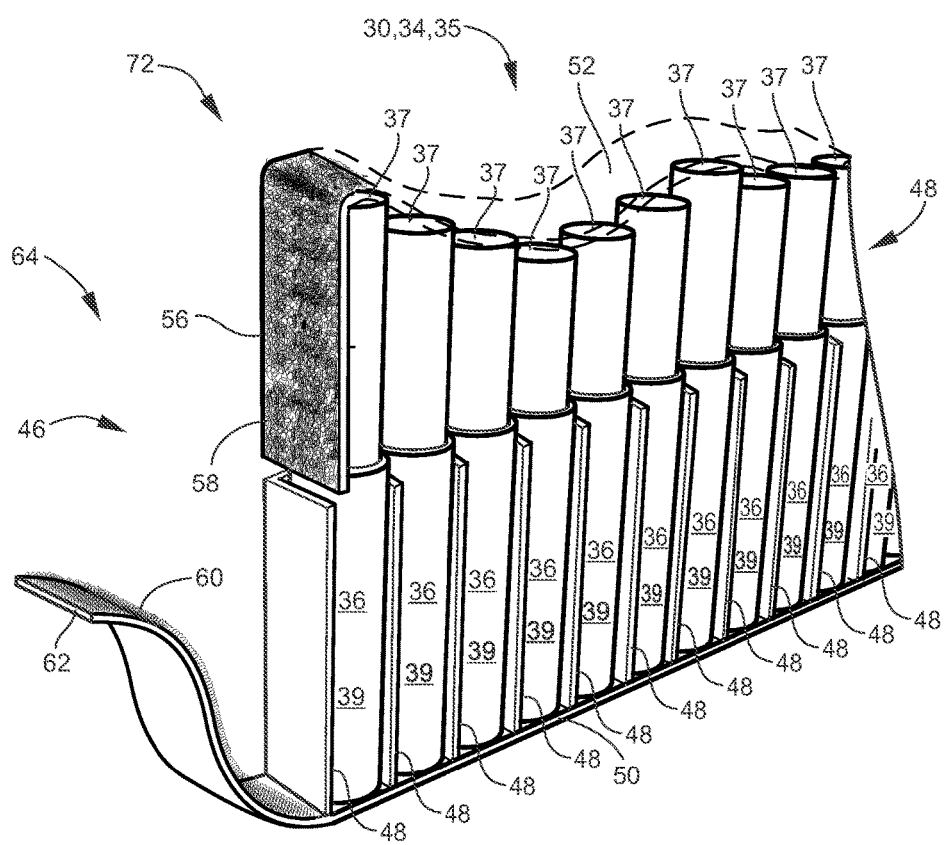
FIG. 11 is a partial perspective view of the coil springs piston assembly or coil spring without piston assembly of FIG. 8 with the bottom strip belt disconnected from the top strip belt and the coil spring piston units or coil spring without piston units extended to an expanded position with various force locations of the constant upward push force.

Referring now specifically to FIGS. 1C, 2-3 and 7, one feature of cervical collar device 10 may be that when coil springs piston assembly 34 or coil spring without piston assembly 35 is inserted inside compartment 68 of flexible neck brace 12 (as shown in FIG. 7), flexible neck brace 12 may be configured for placement around a user's neck 28 (as shown in FIG. 2), where each of the top fasteners 56 are configured to be released from each of the bottom fasteners 60 via the first opening 84 and the second opening 86 (as shown in FIGS. 8-13), thereby releasing top strip belt 50 from bottom strip belt 52 and releasing the plurality of coil spring piston units 36 or coil spring without piston units 39 to expanded position 72 (as shown in FIGS. 10, 11 and 12) for providing the constant upward push force 32 (as shown in FIG. 3).

Flexible neck brace 12 may be made from any desired materials or parts configured for creating cervical collar device 10 for providing constant upward push force 32. In select embodiments, flexible neck brace 12 may include stretchable fabric 74 with foam lining 76. As shown in the Figures, stretchable fabric 74 with foam lining 76 may be positioned on, in or around, inner side 78, top 14, and bottom 16. This configuration with stretchable fabric 74 on inner side 78, top 14, and bottom 16, may allow for flexible neck brace 12 to expand and contract with coil spring piston assembly 34 or coil spring without piston assembly 35. In select embodiments, flexible neck brace 12 may include a hard, porous and flexible plate 80 on an outer side 82. Plate 80 may provide some rigidity to flexible neck brace 12 and allow for first opening 84 with first zipper 66 and second opening 86 with second zipper 70 for accessing compartment 68. As such, plate 80 may include first opening 84 with first zipper 66 on first side 20 configured for accessing compartment 68 inside flexible neck brace 12. Plate 80 may also include second opening 86 with second zipper 70 on second side 22 configured for accessing compartment 68 inside flexible neck brace 12.

As shown in FIGS. 1A, 1B, 1C, 4-5, 7, and 12-13, another feature of cervical collar device 10 may be the inclusion of first fastener 88 and second fastener 90. First fastener 88 may be approximate first side 20. Second fastener 90 may be located on flap 91 approximate second side 22. Whereby, when user 26 wraps flexible neck brace 12 around neck 28 of user 26, flap 91 with second fastener 90 may be configured to extend over first side 20 with first zipper 66 and second side 22 with second zipper 70 and attach to first fastener 88 for securing flexible neck brace 12 around neck 28 of user 26, or vice versa. Protective tab 93 may be positioned on first side 20 (as shown in the Figures), or second side 22. Protective tab 93 may be configured for protecting neck 28 of user 26 from first side 20 with first zipper 66 and second side 22 with second zipper 70. Whereby, when user 26 wraps flexible neck brace 12 around neck 28 of user 26, protective tab 93 may be configured to extend behind first side 20 with first zipper 66 and second side 22 with second zipper 70 for protecting neck 28 of user 26.

Referring specifically to FIG. 2, another feature of cervical collar device 10 may be that flexible neck brace 12 may be configured to be worn around the user's neck 28 by slightly compressing it and placing it around the neck 28.

Referring specifically to FIG. 3, another feature of cervical collar device 10 may be that flexible neck brace 12 may be configured to be placed on top of clavicle bones 94 and shoulders 96 of the user 26, which are non-movable, whereby flexible neck brace 12 may provide constant upward push force 32 on lower jaw 98, mastoid bone 100 and base of skull 102 at the various force locations 37 (see FIG. 12), thereby causing the cervical spine structures, including the vertebrae, all neck muscles, nerves and vessels to be under a constant stretch which may with time promote and enhance a potential growth and lengthening of the cervical structure in children and young adults, and also may prevent the shortening of the neck due to osteoporosis of cervical vertebrae in older adults. Another feature of cervical collar device 10 may be that it can provide relief of muscle spasm of the neck. Another feature of cervical collar device 10 may be that it can alleviate pain caused by a cervical spine disc or a pinched nerve. Another feature of cervical collar device 10 may be that it can promote lengthening of the neck in children and young adults. Another feature of cervical collar device 10 may be that it can prevent shortening of the neck. Another feature of cervical collar device 10 may be that it can prevent shortening of the neck caused by osteoporosis in older adults. Another feature of cervical collar device 10 may be that it can relieve muscle spasm of the neck by stretching the muscles. Another feature of cervical collar device 10 may be that it can alleviate the pain caused by cervical disc or pinched nerve by stretching the cervical spine and increasing the spaces between the vertebrae, thus, relieving the pressure on the nerve. Another feature of cervical collar device 10 may be that the cervical collar device does not require any power source to function. Another feature of cervical collar device 10 may be that the cervical collar device has no need for maintenance. Another feature of cervical collar device 10 may be that cervical collar device 10 may be washable and dryable. Another feature of cervical collar device 10 may be that the constant upward push force device may be replaceable.

Figure 14:
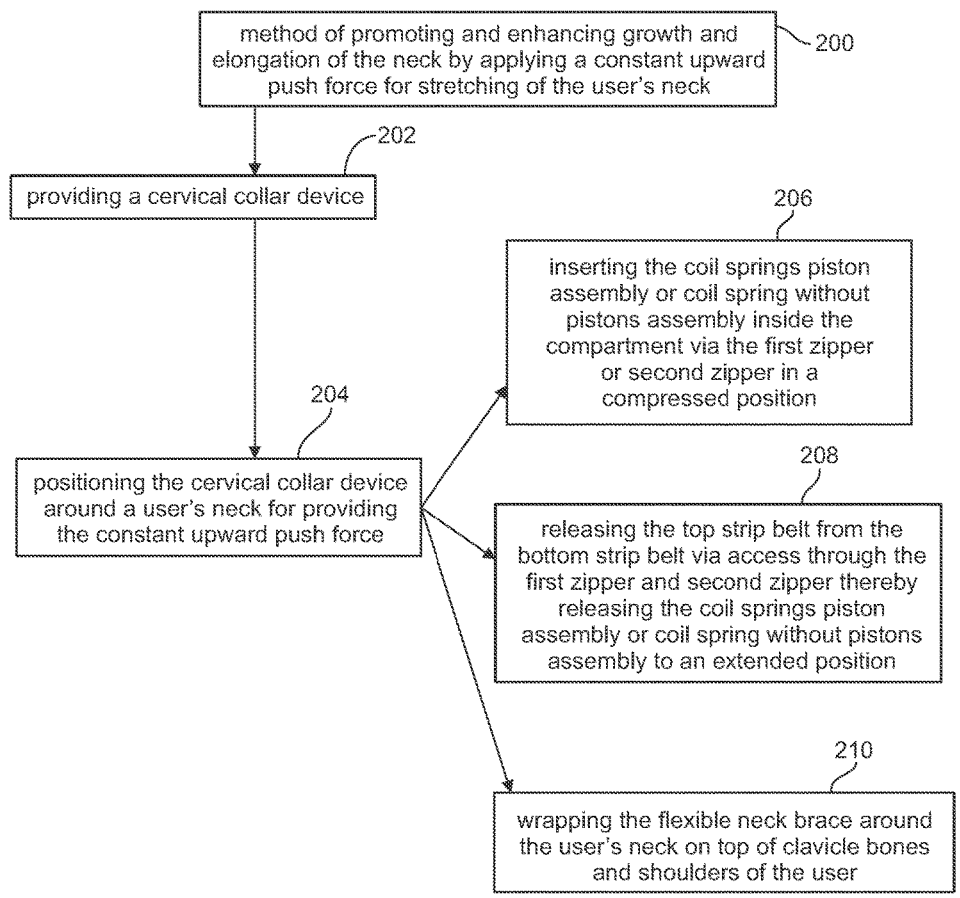
FIG. 14 is a flow chart of the method of promoting and enhancing growth and elongation of the neck by applying a constant upward push force for stretching of the user's neck according to select embodiments of the instant disclosure.

Referring now to FIG. 14, in another aspect, the instant disclosure provides method 200 of promoting and enhancing growth and elongation of the neck 28 by applying constant upward push force 32 for stretching of the user's neck 28. Method 200 of promoting and enhancing growth and elongation of the neck 28 by applying constant upward push force 32 for stretching of the user's neck 28 may generally include step 202 of providing cervical collar device 10 in any of the various embodiments shown and/or described herein, including at least the flexible neck brace 12 with constant upward push force device 30. As such, method 200 of promoting and enhancing growth and elongation of the neck 28 by applying constant upward push force 32 for stretching of the user's neck 28 may also include step 204 of positioning cervical collar device 10 around user's neck 28 for providing constant upward push force 32.

In select embodiments of method 200 of promoting and enhancing growth and elongation of the neck 28 by applying constant upward push force 32 for stretching of the user's neck 28, step 204 of positioning cervical collar device 10 around user's neck 28 for providing constant upward push force 32 may include the steps of: step 206 of inserting the coil springs piston assembly 34 or coil spring without piston assembly 35 inside compartment 68 via first opening 84 with first zipper 66 or second opening 86 with second zipper 70 in compressed position 54; step 208 of releasing top strip belt 50 from bottom strip belt 52 via access through first zipper 66 and second zipper 70 thereby releasing coil springs piston assembly 34 or coil spring without piston assembly 35 to expanded position 72; and step 210 of wrapping flexible neck brace 12 around the user's neck 28 on top of clavicle bones 94 and shoulders 96 of the user 26, which are non-movable, whereby flexible neck brace 12 provides constant upward push force 32 on lower jaw 98, mastoid bone 100 and base of skull 102 of user 26 at the various force locations 37, thereby causing the cervical spine structures, including the vertebrae, all neck muscles, nerves and vessels to be under a constant stretch which will with time promote and enhance a potential growth and lengthening of the cervical structure in children and young adults, and also prevent the shortening of the neck due to osteoporosis of cervical vertebrae in older adults.

In sum, the instant disclosure may be directed to an improvised cervical collar designed 10 to provide constant upward push force 32. Constant upward push force 32 may be provided by cervical collar device 10 to promote and enhance growth and elongation of the neck 28 by applying constant upward push force 32 and stretching of the neck 28 of the user 26. Cervical collar device 10 may have to be worn a long enough time to achieve the intended benefits. Cervical collar device 10 provides an innovation utilizing a special built in mechanism, coil springs pistons assembly 34 or coil spring without piston assembly 35, to promote and enhance growth and elongation of the neck 28 by applying constant upward push force 32 and stretching of the neck 28. Therefore, it may have to be worn a long enough time to achieve these intended benefits. Cervical collar device 10 may also has two immediate intended benefits, such as the relief of muscle spasm of the neck 28 and alleviating the pain cause by a cervical spine disc or a pinched nerve. As examples, cervical collar device may be used to promote lengthening of the neck 28 if used properly and for long duration in children and young adults. Cervical collar device 10 may also prevent shortening of the neck 28, which is usually caused by osteoporosis in older adults. Cervical collar device 10 may also relieve muscle spasm of the neck 28 by stretching the muscles. Cervical collar device 10 may also be used to alleviate the pain caused by cervical disc or pinched nerve by stretching the cervical spine and increasing the spaces between the vertebrae, thus, relieving the pressure on the nerve. User 26 may feel the comfortable constant upward push force 32 on the lower jaw, the mastoid bone and the base of skull at the various force locations 37, causing the cervical spine structures, including the vertebrae, all neck muscles, nerves and vessels to be under a constant stretch which may with time promote and enhance a potential growth and lengthening of the cervical structure in children and young adults. Cervical collar device 10 may also prevent the shortening of the neck 28 due to osteoporosis of cervical vertebrae in older adults.

Another important point must be emphasized that the instant disclosure of cervical collar device 10 with constant upward push force 32 is not intended to be used in neck trauma or head injury.

The elongation of neck 28 may depend on three factors:
1) The age of the person and the growth level of tissue structures of the neck (A). Therefore, it is more effective in children;
2) The amount of the constant upward push force (CUPF) (F); and
3) The time duration when the cervical collar device 10 is worn (T).

This will create an equation of L is proportional to FT/A, where L is total length gained, F is total forces of the springs, T is the time duration, and A is the age of the user. It may be recommended that cervical collar device 10 be worn as many hours as desired during day and night. However, it may not be advised to wear cervical collar device 10 while chewing gum, drinking or eating to avoid chocking. The recommended constant upward push force 32 which is (F), may have the range from (5-15 lb PSI), or more psi, or as much force as required to fulfill its desired functions, which may depend on the age of the user and tolerance. Coil spring piston assembly 34 can be made replaceable in different strengths for the same person.

The instant disclosure recognizes that the sum of constant upward push forces 32 harnessed from cervical collar device 10 may be the plurality of all the forces of coil springs piston units 36 or coil spring without piston units 39, and the total constant upward push force 32 (vector) must be equal or slightly more than the weight of the head of user 26 to achieve the maximum benefit of cervical collar device 10. To measure the PSI of the coil spring piston unit 36 or the coil spring without piston unit 39, the PSI=minimal weight (in lb) required to fully compress the coil spring 42 or extended coil spring 43, divided by the square area of the upper orifice of the coil spring or extended coil spring in square inches.

The cloth, cushion and cover of the cervical collar device 10 may be made of washable and dryable fabric materials. Cervical collar device 10 may be made in different sizes and styles to suit all users' fashion, styles and desires, and also to fit all necks. Suggestions for sizes of cervical collar device 10 may be, but are not limited to:
1) mini size=10 inch length 24×3 inch height 18, with a piston length of 2.8 in of upper cylinder piston 38, a piston diameter of 5 mm of upper cylinder piston 38, a cylinder length of 2.8 in of hollow lower cylinder 40, a cylinder diameter of 6 mm of hollow lower cylinder 40, coil spring 42 outer diameter of 5 mm, coil spring 42 length of 2.8 in, total coil spring piston unit length of 3 in while in a compressed position. Whereas, for the coil spring without piston assembly 35 the measurement are as follow: 10 inch length 24×3 inch height 18, with no piston, and hollow lower cylinder 40 length 2.8 in, cylinder diameter 6 mm, and extended coil spring 43 length is 5.6 inch (double the cylinder length), extended coil spring outer diameter is 5 mm, the total coil spring without piston unit length, while in a compressed position is 3 in.
2) small size=12 inch length 24×3.5 inch height 18, with a piston length of 3.3 in of upper cylinder piston 38, a piston diameter of 5 mm of upper cylinder piston 38, a cylinder length of 3.3 in of hollow lower cylinder 40, a cylinder diameter of 6 mm of hollow lower cylinder 40, coil spring 42 outer diameter of 5 mm, coil spring 42 length of 3.3 in, total coil spring piston unit length while in a compressed position is 3.5 in. Whereas, for the coil spring without piston assembly 35 the measurement are as follow: 12 inch length 24×3.5 inch height 18, with no piston, and hollow lower cylinder 40 length 3.3 in, cylinder diameter 6 mm, and extended coil spring 43 length is 6.6 inch (double the cylinder length), extended coil spring outer diameter is 5 mm, the total coil spring without piston unit length, while in a compressed position is 3.5 in.
3) Medium size=14 inch length 24×4 inch height 18, with a piston length of 3.8 in of upper cylinder piston 38, a piston diameter of 5 mm of upper cylinder piston 38, a cylinder length of 3.8 in of a hollow lower cylinder 40, a cylinder diameter of 6 mm of a hollow lower cylinder 40, coil spring 42 outer diameter of 5 mm, coil spring 42 length of 3.8 inch, total coil spring piston unit length while in a compressed position is 4 in. Whereas, for the coil spring without piston unit 35 the measurements are as follow: 14 inch length 24×4 inch height 18, with no piston, and a hollow lower cylinder 40 length 3.8 in, cylinder diameter 6 mm, and extended coil spring 43 length is 7.6 inch (double the cylinder length), extended coil spring outer diameter is 5 mm, the total coil spring without piston unit length while in a compressed position is 4 in.

4) large size=16 inch length 24×4.5 inch height 18, with a piston length of 4.3 in of upper cylinder piston 38, a piston diameter of 5 mm of upper cylinder piston 38, a cylinder length of 4.3 in of hollow lower cylinder 40, a cylinder diameter of 6 mm of hollow lower cylinder 40, coil spring 42 outer diameter of 5 mm, coil spring 42 length of 4.3 in, total coil spring piston unit length of 4.5 in., while in a compressed position. Whereas, for the coil spring piston without assembly 35 the measurement are as follow: 16 inch length 24×4.5 inch height 18, with no piston, and hollow lower cylinder 40 length 4.3 in, cylinder diameter 6 mm, and extended coil spring 43 length is 8.6 inch (double the cylinder length), extended coil spring outer diameter is 5 mm, the total coil spring without piston unit length, while in a compressed position is 4.5 in.

5) X-Large size=18 inch length 24×4.5 inch height 18, with a piston length of 4.3 in of upper cylinder piston 38, a piston diameter of 5 mm of upper cylinder piston 38, a cylinder length of 4.3 in of hollow lower cylinder 40, a cylinder diameter of 6 mm of hollow lower cylinder 40, coil spring 42 outer diameter of 5 mm, coil spring 42 length of 4.3 in, total coil spring piston unit length of 4.5 in., while in a compressed position. Whereas, for the coil spring piston without assembly 35 the measurement are as follow: 18 inch length 24×4.5 inch, height 18, with no piston, and hollow lower cylinder 40 length 4.3 in., cylinder diameter 6 mm, and extended coil spring 43 length is 8.6 inch (double the cylinder length), extended coil spring outer diameter is 5 mm, the total coil spring without piston unit length, while in a compressed position is 4.5 in.

6) XX-Large size=20 inch length 24×4.5 inch height 18, with a piston length of 4.3 in of upper cylinder piston 38, a piston diameter of 5 mm of upper cylinder piston 38, a cylinder length of 4.3 in of hollow lower cylinder 40, a cylinder diameter of 6 mm of hollow lower cylinder 40, coil spring 42 outer diameter of 5 mm, coil spring 42 length of 4.3 in, total coil spring piston unit length of 4.5 in., while in a compressed position. Whereas, for the coil spring piston without assembly 35 the measurement are as follow: 20 inch length 24×4.5 inch, height 18, with no piston, and hollow lower cylinder 40 length 4.3 in., cylinder diameter 6 mm, and extended coil spring 43 length is 8.6 inch (double the cylinder length), extended coil spring outer diameter is 5 mm, the total coil spring without piston unit length, while in a compressed position is 4.5 in. These example sizes may only be a guide, and other sizes can be made to suit all needs. The most likely to change are the diameters of the coil springs, extended coil springs, pistons, and the lower cylinders, which may be in the ranges between 5 mm to 10 mm, or more. However, the lengths of the coil springs, pistons and cylinders may remain the same or change slightly.

In the specification and/or figures, typical embodiments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herein, but is limited only by the following claims.

The invention claimed is:

1. A cervical collar device comprising:
   a flexible neck brace including a top and a bottom with a height therebetween, and a first side and a second side with a length therebetween, where the height and the length of the flexible neck brace is configured for placement around a neck of a user; and
   a constant upward push force device positioned inside said flexible neck brace being configured to provide a constant upward push force between said top and said bottom of said flexible neck brace, wherein the constant upward push force device comprises:
   a coil springs pistons assembly configured to promote and enhance growth and elongation of the neck by applying the constant upward push force for stretching of the neck of the user, the coil springs pistons assembly includes a plurality of coil spring piston units configured to provide the constant upward push force at a plurality of force locations, wherein each of the plurality of coil spring piston units includes:
   an upper cylinder piston;
   a hollow lower cylinder; and
   a coil spring;
   wherein, the upper cylinder piston slides within the hollow lower cylinder, where the upper cylinder piston and the hollow lower cylinder contain the coil spring, where the coil spring is configured to bias the upper cylinder piston from the hollow lower cylinder, whereby the upper cylinder piston is configured to slide into the hollow lower cylinder under pressure and compress the coil spring, and the upper cylinder piston is configured to slide out of the hollow lower cylinder when the pressure is released by the bias provided by the coil spring;
   or
   a coil spring without pistons assembly configured to promote and enhance growth and elongation of the neck by applying the constant upward push force for stretching of the neck of the user, the coil spring without pistons assembly includes a plurality of coil spring units configured to provide the constant upward push force at a plurality of force locations, wherein each of the plurality of coil spring without piston units includes:
   a hollow lower cylinder; and
   an extended coil spring;
   wherein, the extended coil spring is positioned within the hollow lower cylinder, where the extended coil spring is configured to bias out of the hollow lower cylinder, whereby the extended coil spring is configured to compress into the hollow lower cylinder under pressure, and the extended coil spring is configured to extend out of the hollow lower cylinder when the pressure is released;

wherein the coil springs piston assembly or the coil spring without piston assembly includes a flexible housing configured to hold each of the coil spring piston unit or coil spring without pistons units, wherein;
    the flexible housing includes a plurality of partitions configured for confining each of the coil spring piston units or coil spring without piston units between each partition; and
    the flexible housing including a top strip belt and a bottom strip belt configured to connect together around the flexible housing, where the top strip belt and the bottom strip belt are configured to hold the plurality of coil spring piston units or coil spring without piston units in a compressed position before insertion into the flexible neck brace.

2. The cervical collar device of claim 1, wherein the constant upward push force provided by the cervical collar device promotes and enhances growth and elongation of the neck by applying the constant upward push force for stretching of the neck of the user.

3. The cervical collar device of claim 1, wherein:
    the coil springs piston assembly comprises 20 to 40 coil spring piston units configured to provide the constant upward push force at a corresponding 20 to 40 force locations; or
    the coil spring without piston assembly comprises 20 to 40 coil spring without piston units configured to provide the constant upward push force at a corresponding 20 to 40 force locations, wherein the extended coil spring is double the length of the coil spring.

4. The cervical collar device of claim 3, wherein the constant upward push force provided by the coil springs piston assembly or the coil spring without pistons assembly is from 5-15 psi.

5. The cervical collar device of claim 1, wherein the top strip belt including a top fastener at or along portions near both ends and the bottom strip belt including a bottom fastener at or along portions of both ends, where the top fasteners are configured to attach to the bottom fasteners at their respective ends for holding the plurality of coil spring piston units or coil spring without piston units in the compressed position before insertion into the flexible neck brace.

6. The cervical collar device of claim 5, wherein the top fastener and the bottom fastener are hook and loop type fasteners.

7. The cervical collar device of claim 5, wherein the flexible neck brace including:
    a first opening with a first zipper on the first side configured for accessing a compartment inside of the flexible neck brace; and
    a second opening with a second zipper on the second side configured for accessing the compartment inside of the flexible neck brace;
    said compartment being sized to receive said coil springs piston assembly or said coil spring without pistons assembly;
    wherein, the coil springs piston assembly or the coil spring without pistons assembly can be inserted into and out of the compartment inside the flexible neck brace via the first opening or the second opening.

8. The cervical collar device of claim 7, wherein, when the coil springs piston assembly or the coil spring without pistons assembly is inserted inside the compartment of the flexible neck brace, the flexible neck brace is configured for placement around the neck of the user, where each of the top fasteners are configured to be released from each of the bottom fasteners via the first opening with the first zipper and the second opening with the second zipper, thereby releasing the top strip belt from the bottom strip belt and releasing the plurality of coil spring piston units or coil spring without piston units to an expanded position for providing the constant upward push force.

9. The cervical collar device of claim 1, wherein the flexible neck brace includes:
    a stretchable fabric with a foam lining an inner side, the top, and the bottom;
    a hard, porous and flexible plate on an outer side, said plate including:
        a first opening with a first zipper on the first side configured for accessing a compartment inside the flexible neck brace; and
        a second opening with a second zipper on the second side configured for accessing the compartment inside the flexible neck brace;
    a first fastener approximate the first side;
    a second fastener located on a flap approximate the second side;
    whereby, when the user wraps the flexible neck brace around the neck of the user, the flap with the second fastener is configured to extend over the second zipper, the second side, and the first side with the first zipper, where it is configured to attach to the first fastener for securing the flexible neck brace around the neck of the user; and
    a protective tab as an extension of the first side configured for protecting the neck of the user from the first side with the first zipper and the second side with the second zipper;
    whereby, when the user wraps the flexible neck brace around the neck of the user, the protective tab is configured to extend behind the first side with the first zipper and the second side with the second zipper for protecting the neck of the user.

10. The cervical collar device of claim 9, wherein the first fastener and the second fastener are hook and loop type fasteners configured to secure to one another.

11. The cervical collar device of claim 1, wherein the flexible neck brace is configured to be worn around the neck of the user by slightly compressing it and placing it around the neck.

12. The cervical collar device of claim 1, wherein the flexible neck brace is configured to be placed on top of clavicle bones and shoulders of the user which are non-movable, whereby the flexible neck brace provides the constant upward push force on a lower jaw, a mastoid bone and a base of skull at various force locations, thereby causing cervical spine structures, including vertebrae, all neck muscles, nerves and vessels to be under a constant stretch which will with time promote and enhance a potential growth and lengthening of the cervical structure in children and young adults, and also prevents the shortening of the neck due to osteoporosis of cervical vertebrae in older adults.

13. The cervical collar device of claim 1, wherein the cervical collar device is adapted to:
    relief of muscle spasm of the neck;
    alleviating of pain caused by cervical spine discs or pinched nerves;
    promotes lengthening of the neck in children and young adults;
    prevents shortening of the neck;
    prevents shortening of the neck caused by osteoporosis in older adults;

relieves muscle spasm of the neck by stretching muscles;
alleviates the pain caused by cervical disc or pinched nerve by stretching a cervical spine and increasing spaces between vertebrae, thus, relieving pressure on nerves; or
combinations thereof.

14. The cervical collar device of claim 1, wherein:
the cervical collar device does not require any power source to function;
the cervical collar device has no need for maintenance;
the cervical collar device is washable and dryable; and
the constant upward push force device is replaceable.

15. A cervical collar device comprising:
a flexible neck brace including:
   a top and a bottom with a height therebetween;
   a first side and a second side with a length therebetween;
   where the height and the length of the flexible neck brace is configured for placement around a neck of a user;
   a stretchable fabric with a foam lining on an inner side, the top, and the bottom;
   a hard, porous and flexible plate on an outer side, said plate including:
      a first opening with a first zipper on the first side configured for accessing a compartment inside the flexible neck brace; and
      a second opening with a second zipper on the second side configured for accessing the compartment inside the flexible neck brace;
   a first fastener approximate the first side;
   a second fastener located on a flap approximate the second side;
   whereby, when the user wraps the flexible neck brace around the neck of the user, the flap with the second fastener is configured to extend over the second zipper, the second side, and the first side with the first zipper, where it is configured to attach to the first fastener for securing the flexible neck brace around the neck of the user; and
   a protective tab as an extension to the first side configured for protecting the neck of the user from the first end with the first zipper and the second side with the second zipper;
   whereby, when the user wraps the flexible neck brace around the neck of the user, the protective tab is configured to extend behind the first side with the first zipper and the second side with the second zipper for protecting the neck of the user; and
a constant upward push force device positioned inside said flexible neck brace being configured to provide a constant upward push force between said top and said bottom of said flexible neck brace, wherein the constant upward push force device is a coil springs pistons assembly or a coil springs without piston assembly configured to promote and enhance growth and elongation of the neck by applying the constant upward push force for stretching of the neck of the user;
wherein the coil springs pistons assembly includes a plurality of coil spring piston units configured to provide the constant upward push force at a plurality of force locations, wherein each of the plurality of coil spring piston units includes:
   an upper cylinder piston;
   a hollow lower cylinder; and
   a coil spring;
   wherein, the upper cylinder piston slides within the hollow lower cylinder, where the upper cylinder piston and the hollow lower cylinder contain the coil spring, where the coil spring is configured to bias the upper cylinder piston from the hollow lower cylinder, whereby the upper cylinder piston is configured to slide into the hollow lower cylinder under pressure and compress the coil spring, and the upper cylinder piston is configured to slide out of the hollow lower cylinder when the pressure is released by the bias provided by the coil spring;
wherein the coil spring without pistons assembly includes a plurality of coil spring units configured to provide the constant upward push force at a plurality of force locations, wherein each of the plurality of coil spring without piston units includes:
   a hollow lower cylinder; and
   an extended coil spring being double the length of the coil spring of the coil springs piston units;
   wherein, the extended coil spring is positioned within the hollow lower cylinder, where the extended coil spring is configured to bias out of the hollow lower cylinder, whereby the extended coil spring is configured to compress into the hollow lower cylinder under pressure, and the extended coil spring is configured to extend out of the hollow lower cylinder when the pressure is released;
wherein the coil springs piston assembly or the coil spring without piston assembly includes a flexible housing configured to hold each of the coil spring piston units or coil spring without piston units;
   the flexible housing includes a plurality of partitions configured for confining each of the coil spring piston units or the coil spring without piston units between each partition; and
   the flexible housing including a top strip belt and a bottom strip belt configured to connect together around the flexible housing, where the top strip belt and the bottom strip belt are configured to hold the plurality of coil spring piston units or coil spring without piston units in a compressed position before insertion into the flexible neck brace;
   wherein the top strip belt including a top fastener at or along portions near both ends and the bottom strip belt including a bottom fastener at or along portions near both ends, where the top fasteners are configured to attach to the bottom fasteners at their respective ends for holding the plurality of coil spring piston units or coil spring without piston units in the compressed position before insertion into the flexible neck brace;
wherein the constant upward push force provided by the cervical collar device promotes and enhances growth and elongation of the neck by applying the constant upward push force for stretching of the neck of the user;
wherein the flexible neck brace is configured to be worn around the neck of the user by slightly compressing it and placing it around the neck;
wherein, when the coil springs piston assembly or coil spring without pistons assembly is inserted inside the compartment of the flexible neck brace, the flexible neck brace is configured for placement around the neck of the user, where each of the top fasteners are configured to be released from each of the bottom fasteners via the first opening with the zipper and the second opening with the second zipper, thereby releasing the top strip belt from the bottom strip belt and releasing the plurality of coil spring piston units or coil spring without piston units to an expanded position for providing the constant upward push force; and wherein the flexible neck brace is configured to be placed around the neck of the user on top of clavicle bones and shoulders of the user which are non-movable, whereby the flexible neck brace provides the constant upward push force on a lower jaw, a mastoid bone and a base of skull at the various force locations, thereby causing cervical spine structures, including vertebrae, all neck muscles, nerves and vessels to be under a constant stretch which will with time promote and enhance a potential growth and lengthening of the cervical structure in children and young adults, and also prevents the shortening of the neck due to osteoporosis of cervical vertebrae in older adults.

16. A cervical collar device comprising:

a flexible neck brace including a top and a bottom with a height therebetween, and a first side and a second side with a length therebetween, where the height and the length of the flexible neck brace is configured for placement around a neck of a user; and a constant upward push force device positioned inside said flexible neck brace being configured to provide a constant upward push force between said top and said bottom of said flexible neck brace;

wherein the flexible neck brace includes:

a stretchable fabric with a foam lining an inner side, the top, and the bottom;

a hard, porous and flexible plate on an outer side, said plate including:
  a first opening with a first zipper on the first side configured for accessing a compartment inside the flexible neck brace; and
  a second opening with a second zipper on the second side configured for accessing the compartment inside the flexible neck brace;

a first fastener approximate the first side;

a second fastener located on a flap approximate the second side;

whereby, when the user wraps the flexible neck brace around the neck of the user, the flap with the second fastener is configured to extend over the second zipper, the second side, and the first side with the first zipper, where it is configured to attach to the first fastener for securing the flexible neck brace around the neck of the user; and a protective tab as an extension of the first side configured for protecting the neck of the user from the first side with the first zipper and the second side with the second zipper;

whereby, when the user wraps the flexible neck brace around the neck of the user, the protective tab is configured to extend behind the first side with the first zipper and the second side with the second zipper for protecting the neck of the user.

\* \* \* \* \*